(12) United States Patent
Shafer-Zatko et al.

(10) Patent No.: US 12,336,865 B2
(45) Date of Patent: Jun. 24, 2025

(54) SURGICAL RETENTION FEATURE

(71) Applicant: Lumitex Inc., Strongsville, OH (US)

(72) Inventors: Brandon Shafer-Zatko, Medina, OH (US); R J Hagler, Brecksville, OH (US); Joe Dombrowski, Medina, OH (US); Kevin Friedman, Fairview Park, OH (US); Vedang Kothari, Cleveland, OH (US); Brian Andrich, Medina, OH (US); Alan Greszler, Westlake, OH (US)

(73) Assignee: Lumitex Inc., Strongsville, OH (US)

( * ) Notice: Subject to any disclaimer, the term of this patent is extended or adjusted under 35 U.S.C. 154(b) by 50 days.

(21) Appl. No.: 18/447,382

(22) Filed: Aug. 10, 2023

(65) Prior Publication Data
US 2023/0380925 A1 Nov. 30, 2023

Related U.S. Application Data

(62) Division of application No. 16/569,006, filed on Sep. 12, 2019, now Pat. No. 11,759,282.

(60) Provisional application No. 62/754,650, filed on Nov. 2, 2018.

(51) Int. Cl.
| | | |
|---|---|---|
| A61B 90/30 | (2016.01) |
| A61B 1/018 | (2006.01) |
| A61B 1/07 | (2006.01) |
| A61B 17/02 | (2006.01) |
| A61B 90/35 | (2016.01) |
| F21V 8/00 | (2006.01) |
| A61B 17/00 | (2006.01) |

(52) U.S. Cl.
CPC .............. *A61B 90/35* (2016.02); *A61B 1/018* (2013.01); *A61B 1/07* (2013.01); *A61B 17/02* (2013.01); *G02B 6/0005* (2013.01); *A61B 2017/00876* (2013.01); *A61B 2090/306* (2016.02)

(58) Field of Classification Search
CPC ..................................................... A61B 90/35
See application file for complete search history.

(56) References Cited

U.S. PATENT DOCUMENTS

| | | | |
|---|---|---|---|
| 8,876,709 B2 | 11/2014 | Vayser et al. | |
| 2002/0125721 A1* | 9/2002 | Imaeda | F16L 37/0985 285/305 |
| 2012/0041268 A1* | 2/2012 | Grey | A61B 1/267 600/199 |
| 2012/0116170 A1 | 5/2012 | Vayser et al. | |
| 2014/0276652 A1 | 9/2014 | Gittard | |
| 2019/0350670 A1 | 11/2019 | Grey et al. | |
| 2022/0054720 A1 | 2/2022 | Hajarian et al. | |

* cited by examiner

*Primary Examiner* — Tessa M Matthews
(74) *Attorney, Agent, or Firm* — Renner, Otto, Boisselle & Sklar, LLP

(57) ABSTRACT

A light guide assembly for use with a retractor having a channel for slidably receiving an end portion of a light guide. The light guide assembly includes a light guide having the end portion for slidably inserting into the channel and retentor for releasably holding in position the end portion relative to the retractor.

8 Claims, 30 Drawing Sheets

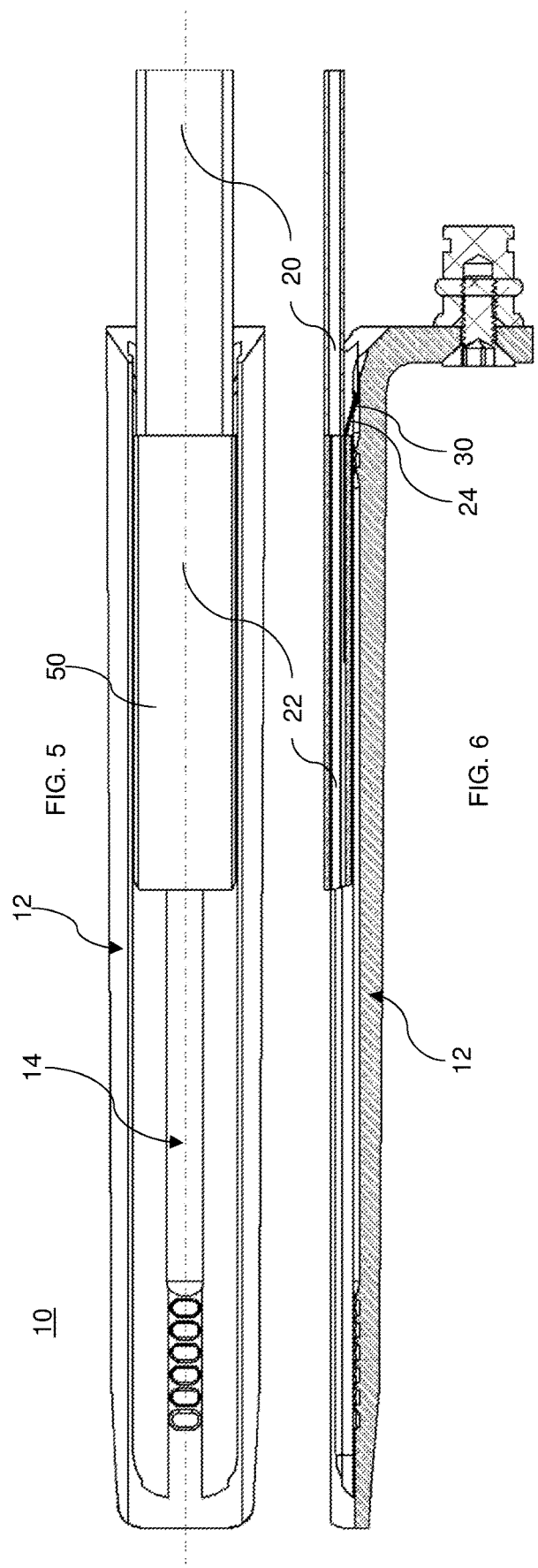

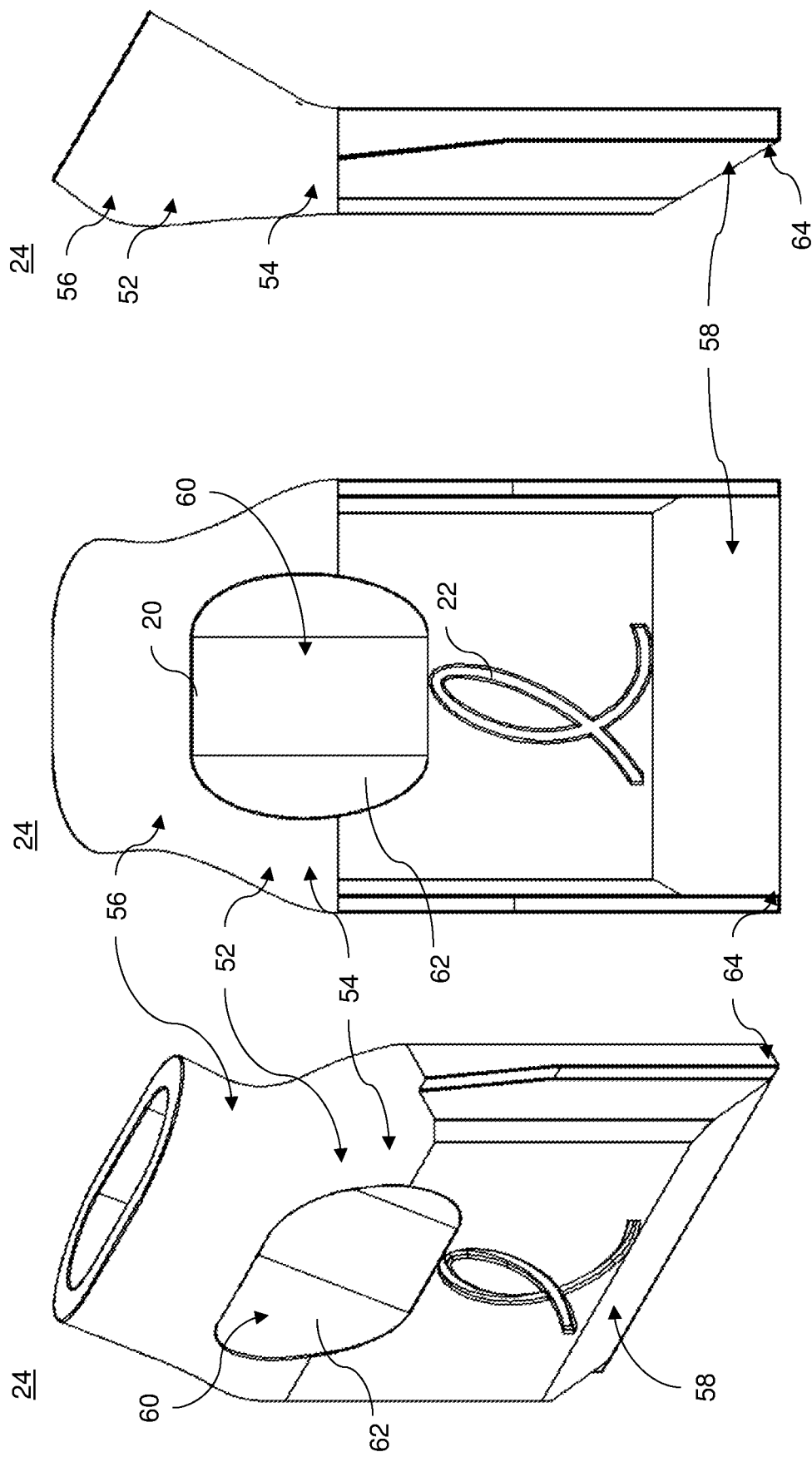

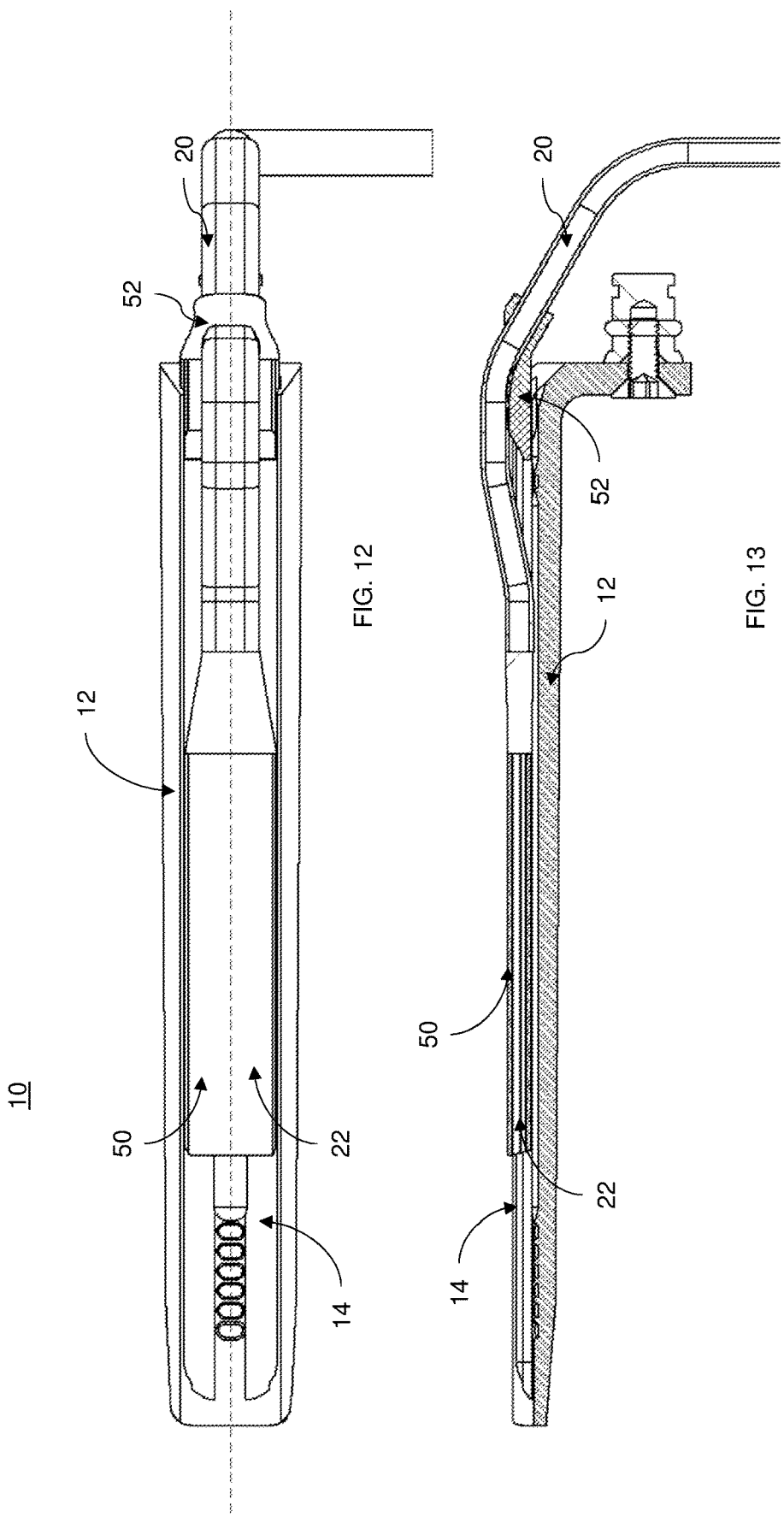

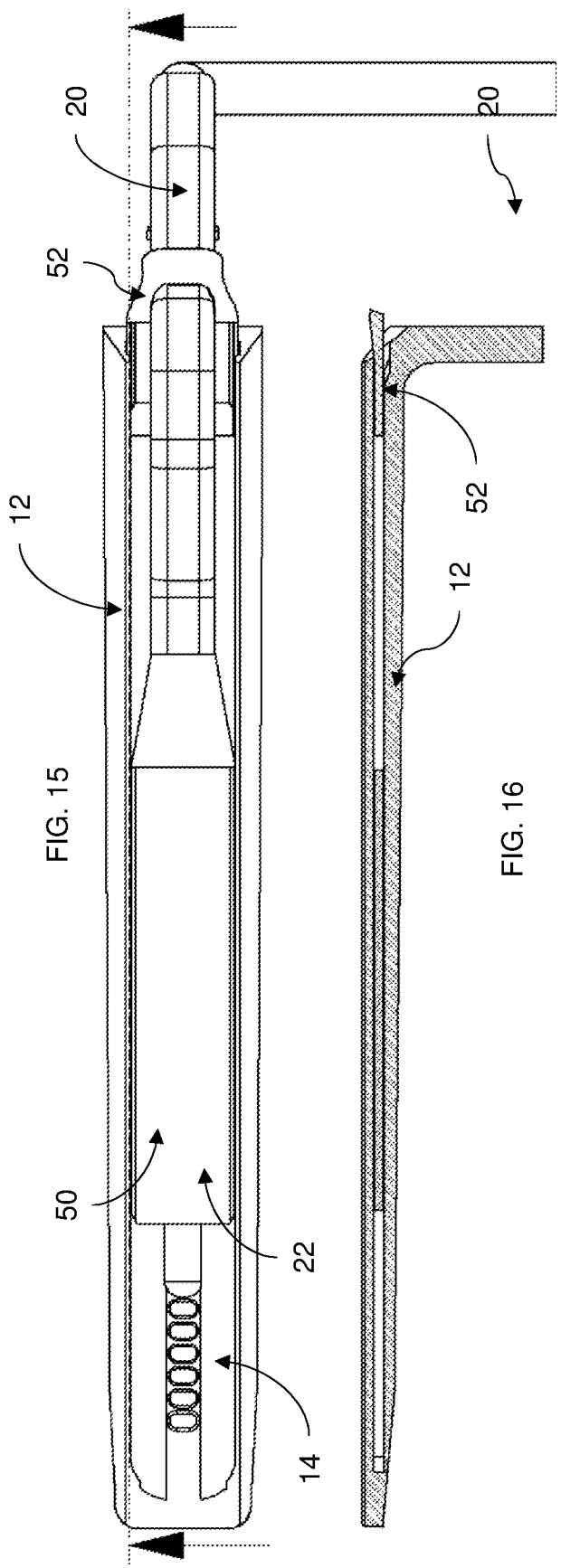

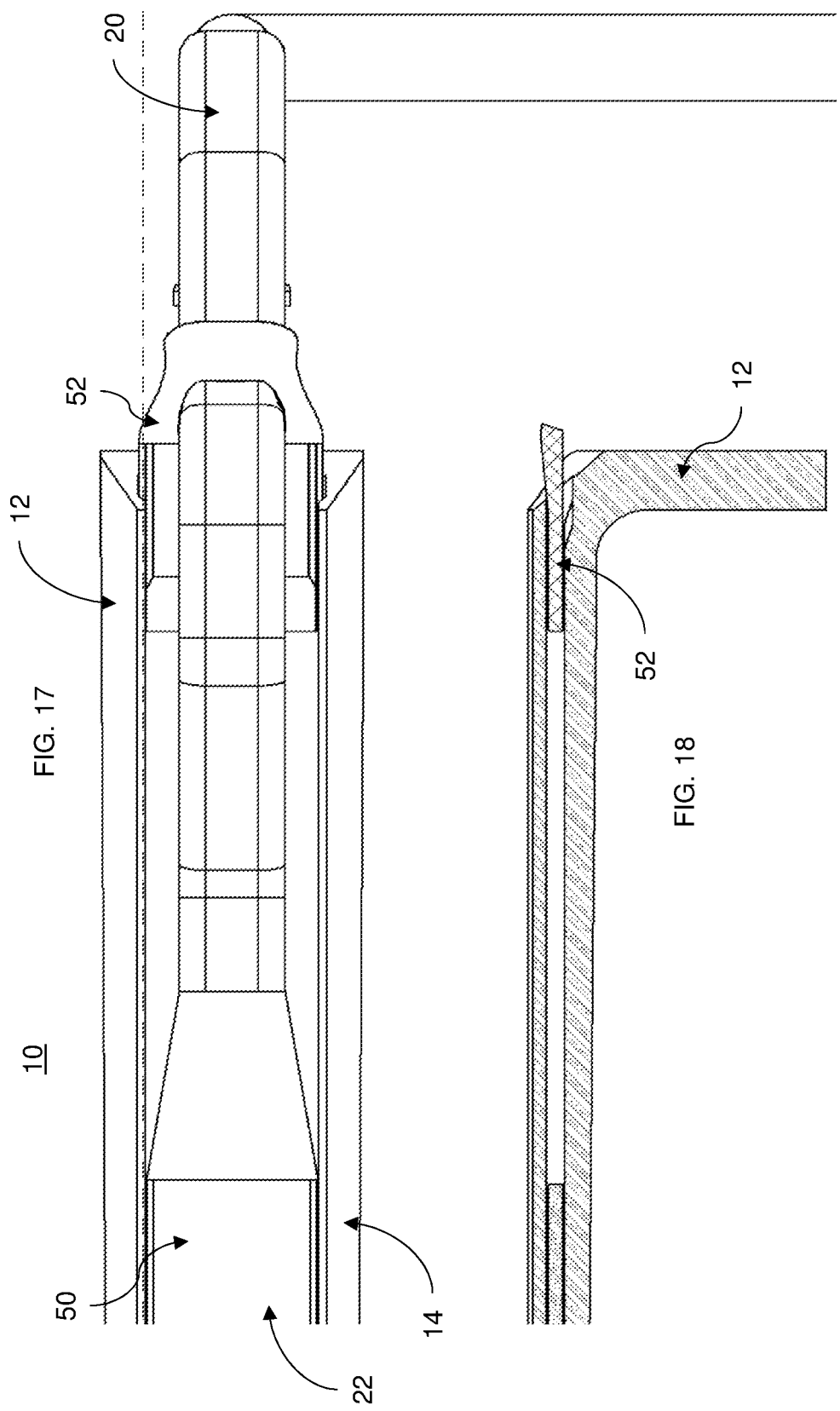

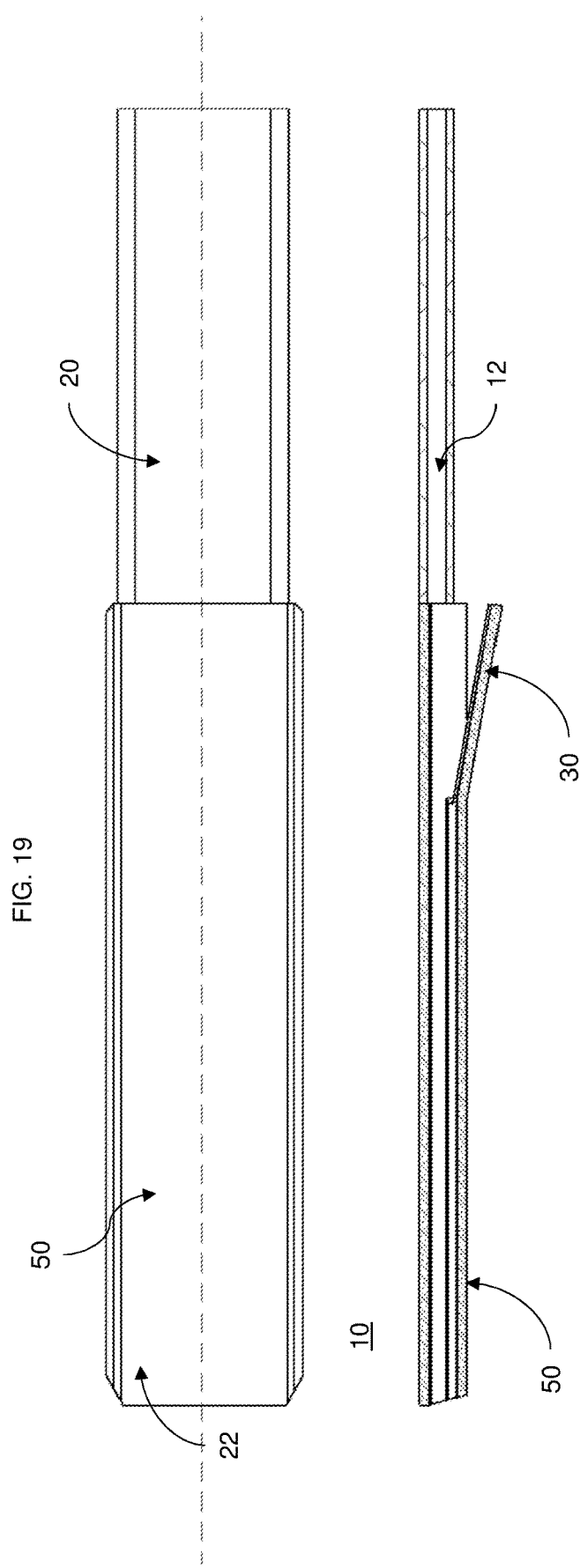

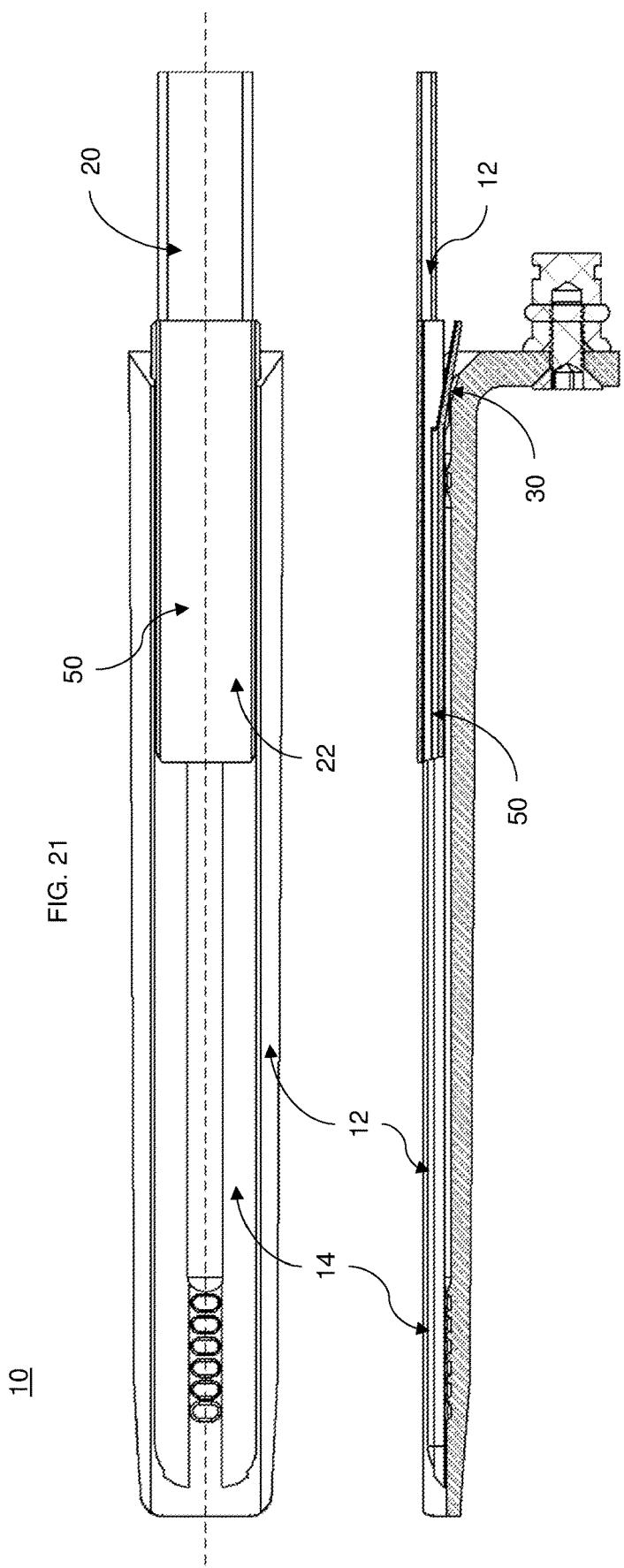

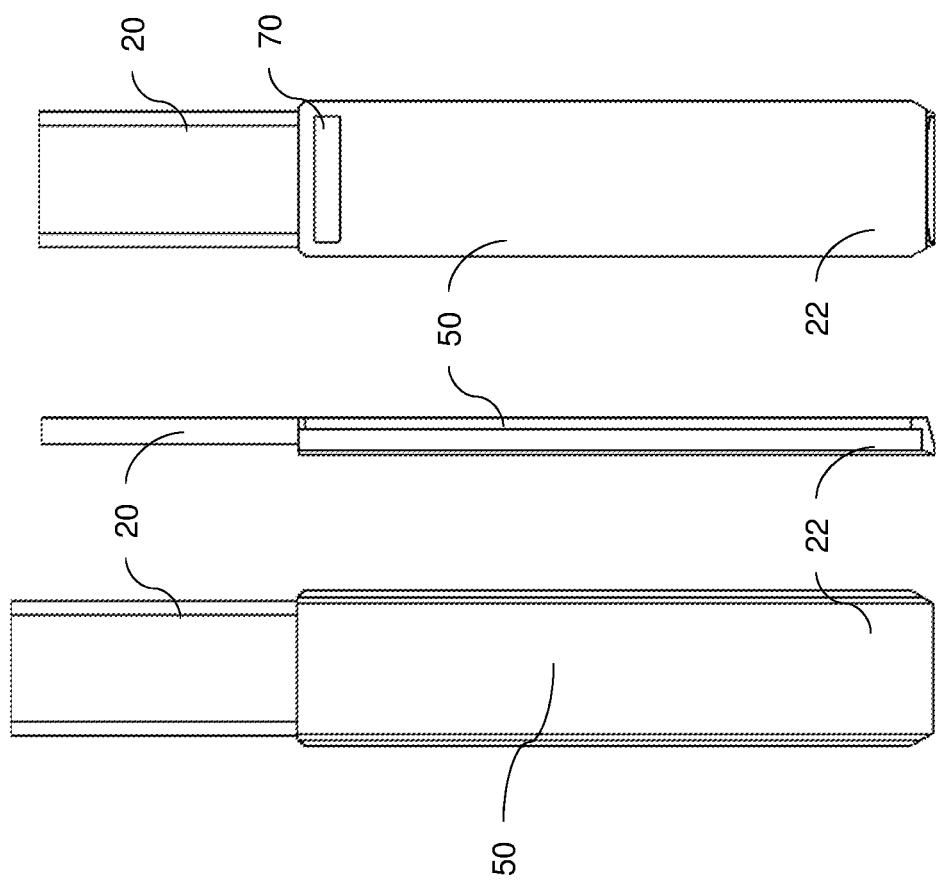

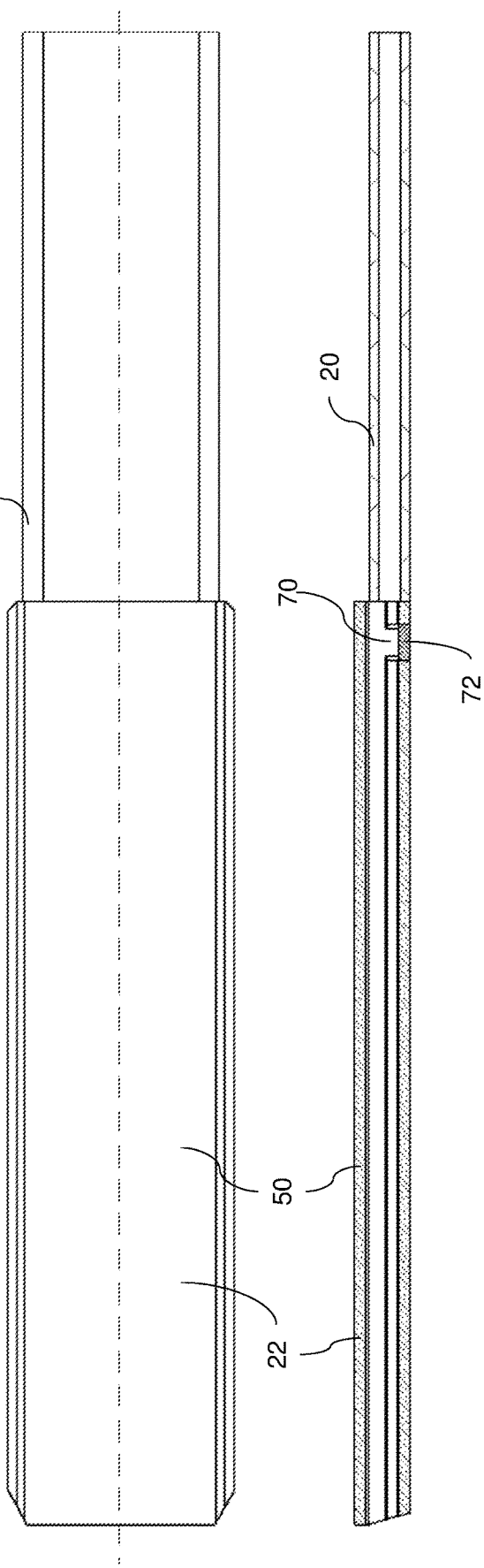

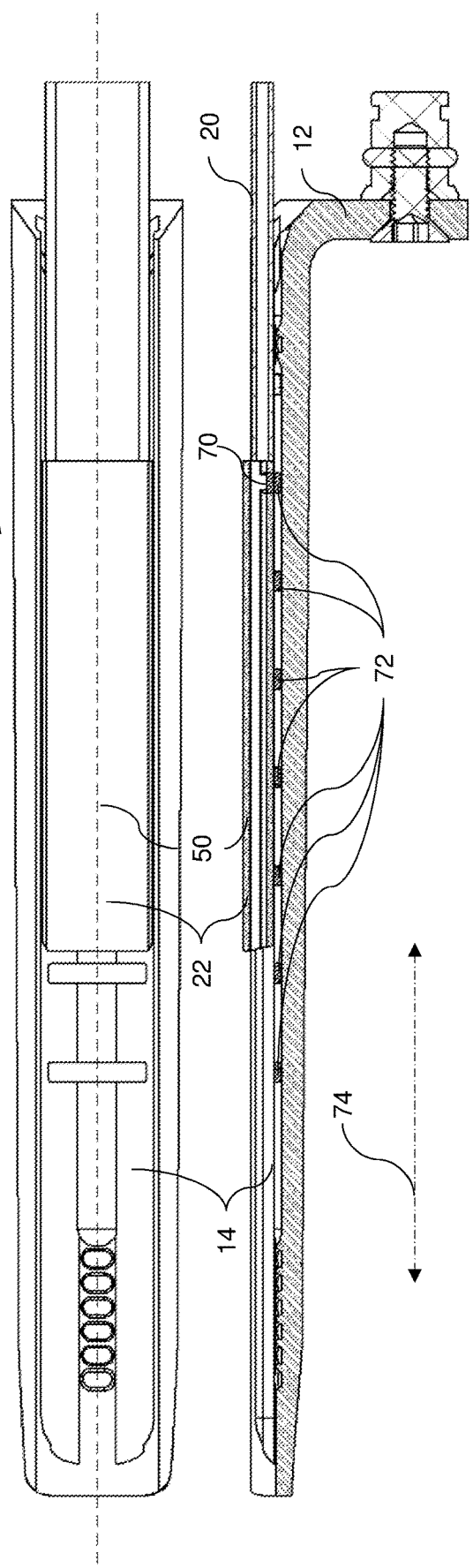

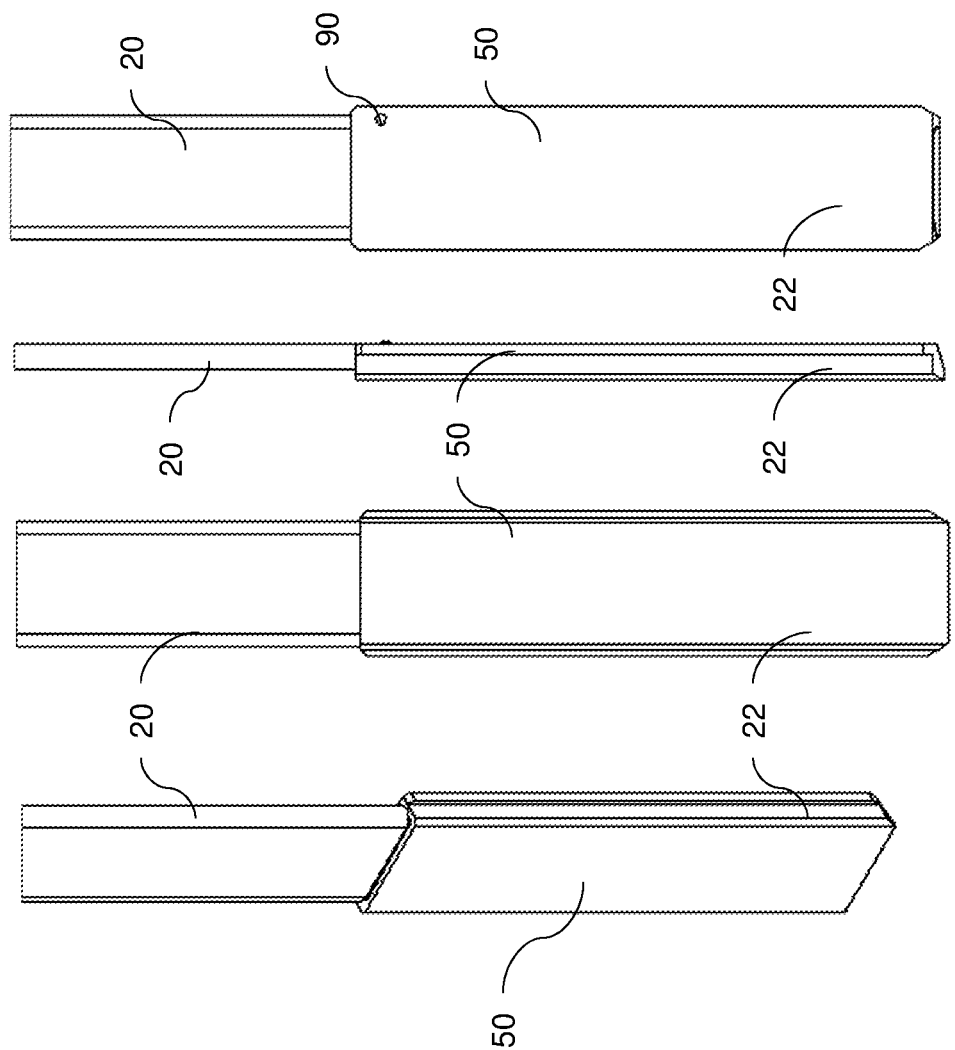

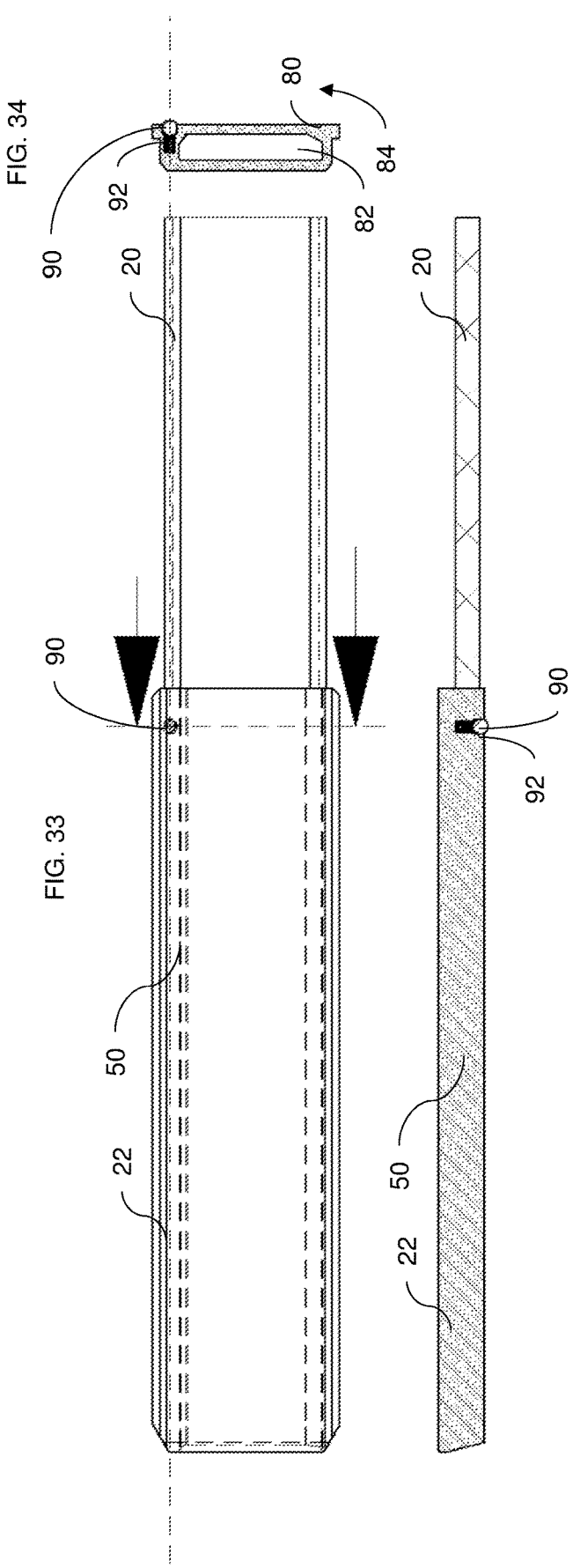

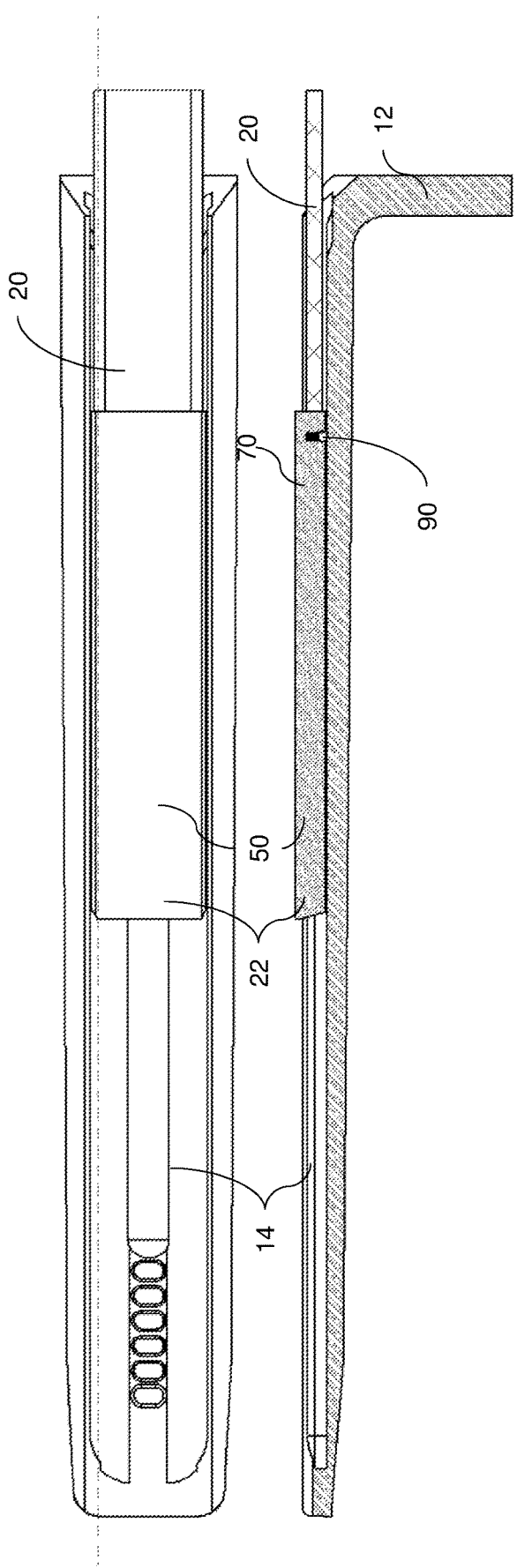

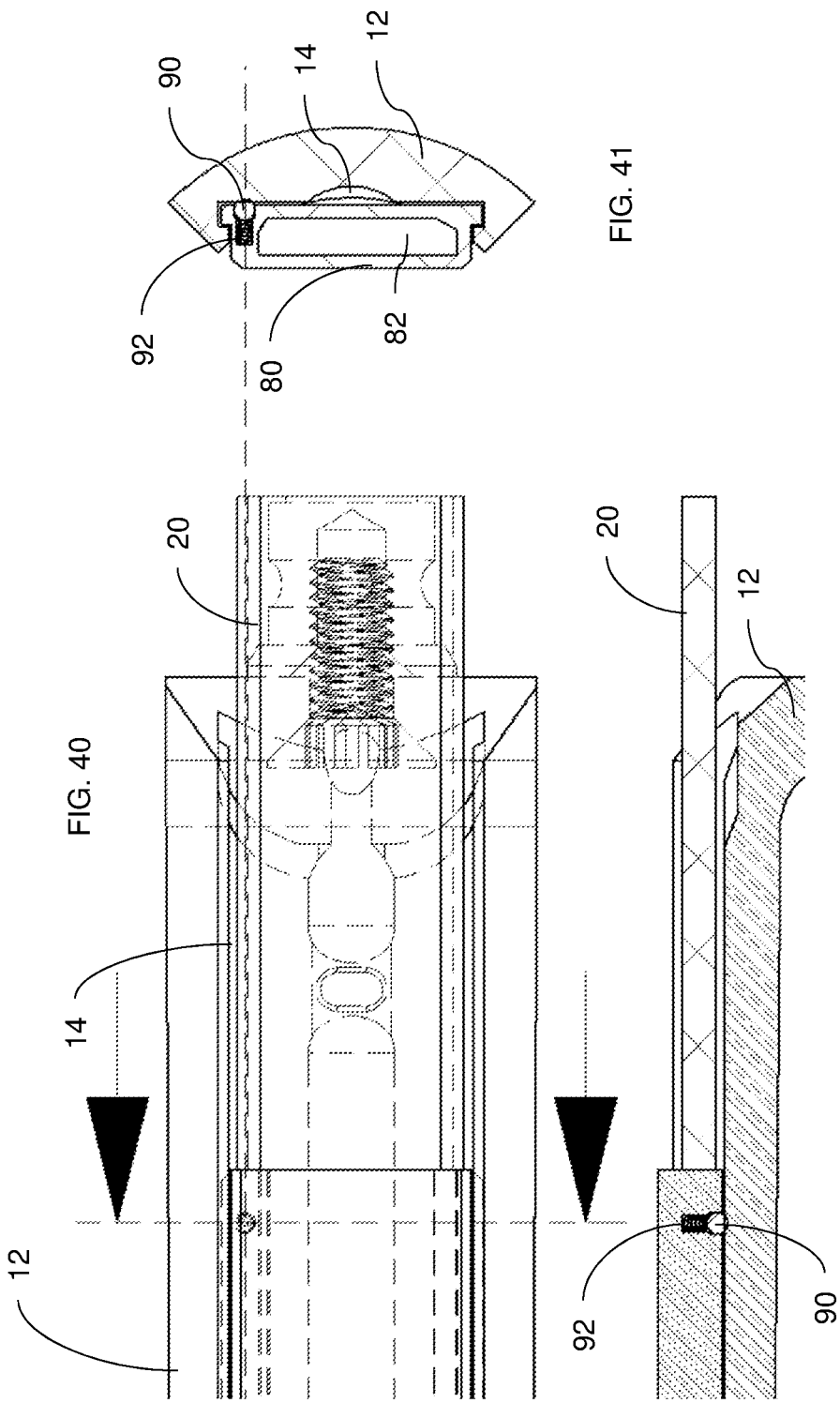

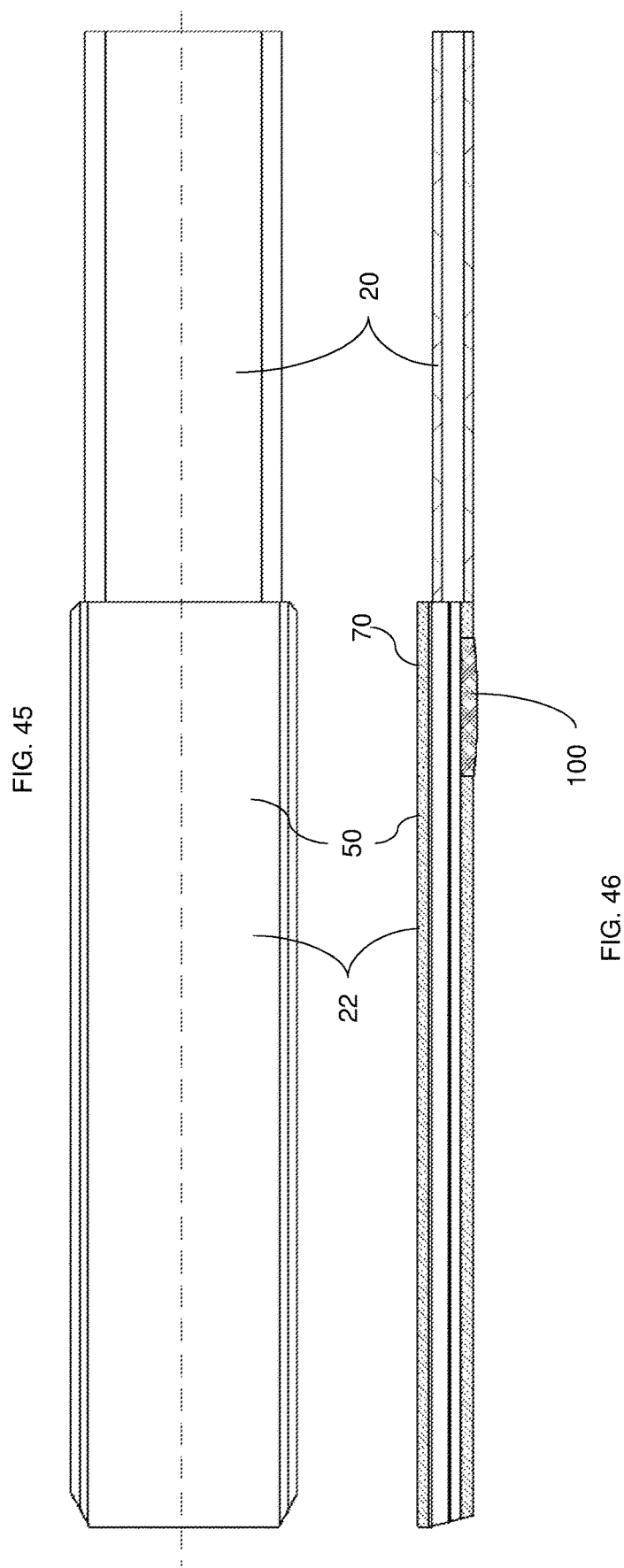

SURGICAL RETENTION FEATURE

RELATED APPLICATIONS

This application claims the benefit of U.S. application Ser. No. 16/569,006 filed on Sep. 12, 2019, which claims priority to United States of America Application No. 62/754,650 filed on Nov. 2, 2018, each of which is herein incorporated by reference in its entirety.

TECHNICAL FIELD

The present disclosure relates generally to surgical illuminators and, in particular, to illuminators for use with surgical retractors.

BACKGROUND

Surgical procedures may employ tissue retractors that provide a surgical corridor through which a surgeon may perform a procedure. These retractors typically consist of two or more elements (blades/paddles) that are connected to a ratcheting frame and are advanced through a surgical incision to the site of operation. This surgical corridor may vary in depth depending on the procedure. Traditional overhead operating room (OR) lighting is typically not ideal for illuminating the surgical corridor, so integrated retractor lighting may be used.

A common form of retractor lighting is a system in which a fiber optic surgical illuminator of a given cross sectional profile slides from above into a channel on the retractor having the same cross sectional profile. This fiber optic illuminator is then connected to a light source, thereby conveying light to the surgical corridor.

SUMMARY

When the surgical illuminators are advanced into the retractor blades, the end distal to the light source is normally set by the operator at a depth along the channel in the retractor blade which provides the most desirable lighting within the surgical corridor.

This depth setting may be upset when the cable connecting the surgical illuminator to the light source is disturbed (e.g., bumped during surgery), requiring the operator to reposition the surgical illuminator during the surgical operation to maintain optimal lighting.

Malleable steel inserts may be used to prevent an illuminator from sliding further into the retractor channel, but the steel insert does not prevent upward motion of the illuminator (i.e., out of the surgical corridor).

The present disclosure provides a light guide assembly for use with a retractor having a channel for slidably receiving an end portion of a light guide. The light guide assembly includes a light guide having the end portion for slidably inserting into the channel and retentor for releasably holding in position the end portion relative to the retractor.

According to one aspect, the disclosure provides a light guide assembly for use with a retractor having a channel. The light guide assembly comprises a light guide having an end portion for slidably inserting into the channel of the retractor. the light guide assembly also includes a retentor for releasably holding in position the end portion relative to the retractor.

Alternatively or additionally, the retentor includes a tab configured to contact the channel during insertion of the end portion into the channel, such that the force required to insert the end portion into the channel is increased.

Alternatively or additionally, the tab has a wedge shape, such that an apex of the tab is located farther from the end portion than a proximal portion of the tab. The apex of the tab is located furthest from the light guide along a radial direction. The proximal portion of the tab is inserted into the channel prior to the apex when the end portion is slidably inserted into the channel.

Alternatively or additionally, upon the tab being slidably inserted into the channel, a force required to further slidably insert the tab into the channel increases until the apex of the tab enters the channel.

Alternatively or additionally, the end portion includes a jacket and the jacket includes the retentor.

Alternatively or additionally, the retentor comprises a wedge configured to contact the channel during insertion of the end portion into the channel, such that the force required to insert the end portion into the channel increases upon the wedge contacting the channel.

Alternatively or additionally, the wedge includes a body having a receiving end and a contacting end. The wedge also includes an aperture in the body located closer to the receiving end than the contacting end. The contacting end includes a contacting tip configured to contact the channel during insertion of the end portion into the channel. The aperture is configured to slide over the light guide, such that: (1) the wedge is positioned distal to the end portion of the light guide such that the end portion enters the channel during insertion into the channel prior to the wedge entering the channel; and (2) the contacting tip enters the channel during insertion into the channel prior to the aperture.

Alternatively or additionally, the body of the wedge has a tapered profile, such that: during insertion into the channel, the body mates to the channel and the tapered profile prevents the wedge from being fully inserted into the channel.

Alternatively or additionally, walls of the aperture are oriented at an angle relative to a front face of the body, such that friction between the light guide and the wedge increases when the wedge is inserted into the channel.

Alternatively or additionally, the wedge includes a living hinge or cantilever spring configured such that a user may squeeze the wedge and/or slide the wedge out of the channel to remove the wedge from the channel.

Alternatively or additionally, the end portion includes a jacket and the jacket includes the retentor. The retentor comprises a first magnet configured to interact with a second magnet included in the channel such that a force required to insert the end portion into the channel is increased by the interaction between the first magnet and the second magnet.

Alternatively or additionally, the first magnet and/or the second magnet has a length along the direction of insertion of the end portion such that, upon the end portion being slidably inserted into the channel, a force required to further slidably insert the end portion into the channel increases.

Alternatively or additionally, the first magnet and/or the second magnet comprises a series of magnets spaced along a longitudinal axis of the jacket.

Alternatively or additionally, the end portion includes a jacket having a wall separating an interior and an exterior of the jacket. The jacket includes the retentor comprising a plunger. The plunger is positioned within an opening of the wall of the jacket such that, when positioned, the plunger extends through the opening of the wall into the exterior of the jacket. Upon the jacket being slidably inserted into the channel, a portion of the plunger extending into the exterior of the jacket interacts with a wall of the channel increasing a force required to further slidably insert the end portion into the channel.

Alternatively or additionally, the end portion includes a jacket. The jacket includes the retentor comprising a button. The button comprises a compressible material that, upon being slidably inserted into the channel, interacts with a wall of the channel increasing a force required to further slidably insert the end portion into the channel.

According to another aspect, the present disclosure provides a retractor assembly including a retractor and a light guide. The retractor includes a blade having a channel for slidably receiving the light guide. The light guide includes a retentor for releasably holding the light guide in position in the channel.

According to a further aspect, the present disclosure provides a method of adjustably positioning a light guide in relation to a retractor having a channel for slidably receiving an end portion of the light guide. The method include the steps of: (1) slidably positioning the light guide into the channel; and (2) using a retentor for releasably maintaining the position of the light guide within the channel.

While a number of features are described herein with respect to embodiments of the invention; features described with respect to a given embodiment also may be employed in connection with other embodiments. The following description and the annexed drawings set forth certain illustrative embodiments of the invention. These embodiments are indicative, however, of but a few of the various ways in which the principles of the invention may be employed. Other objects, advantages and novel features according to aspects of the invention will become apparent from the following detailed description when considered in conjunction with the drawings.

BRIEF DESCRIPTION OF THE DRAWINGS

The annexed drawings, which are not necessarily to scale, show various aspects of the invention in which similar reference numerals are used to indicate the same or similar parts in the various views.

FIGS. 5-7 depicts the light guide assembly of FIGS. 3 and 4 inserted into a channel of a retractor.

FIGS. 9A-9C depict an alternative embodiment of a retention means having a wedge.

FIGS. 12-18 show different views (including cut away views along the dashed lines of the preceding figure) of the light guide assembly of FIG. 10.

FIGS. 19 and 20 show an alternative embodiment of a light guide assembly having a retention means including a tab.

FIGS. 21-23 show different views (including cut away views along the dashed lines of the preceding figure) of the light guide assembly of FIGS. 19 and 20.

FIGS. 24-26 depict an alternative embodiment of a retention means having a magnet.

FIGS. 27-31 show different views (including cut away views along the dashed lines of the preceding figure) of the light guide assembly of FIGS. 24-26.

FIGS. 32A-32D depict an alternative embodiment of a retention means having a plunger.

FIGS. 33-43 show different views (including cut away views along the dashed lines of the preceding figure) of the light guide assembly of FIGS. 32A-32D.

FIGS. 45-49 show different views (including cut away views along the dashed lines of the preceding figure) of the light guide assembly of FIGS. 44A-44D.

DETAILED DESCRIPTION

Figure 1:
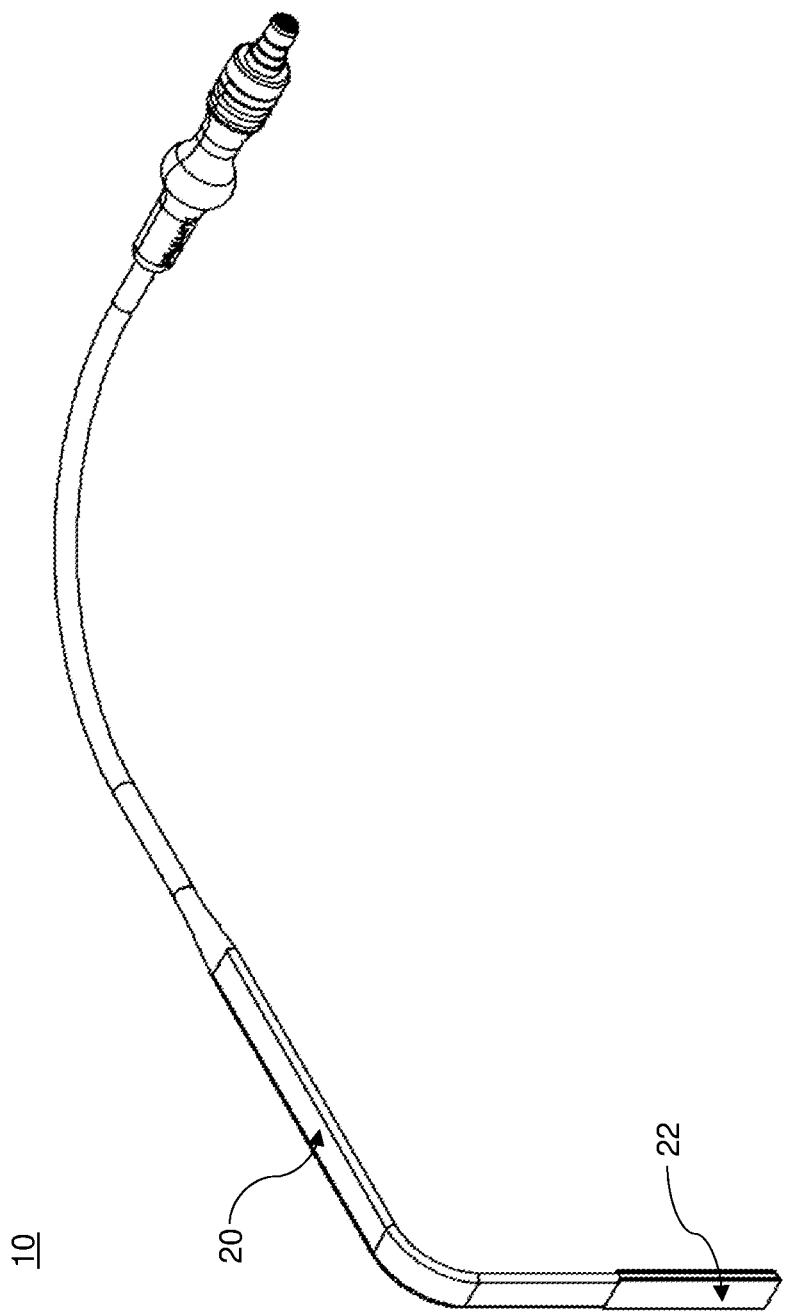
FIG. 1 is an exemplary embodiment of a light guide assembly including a retention means (also referred to as a retentor).
Figure 2:
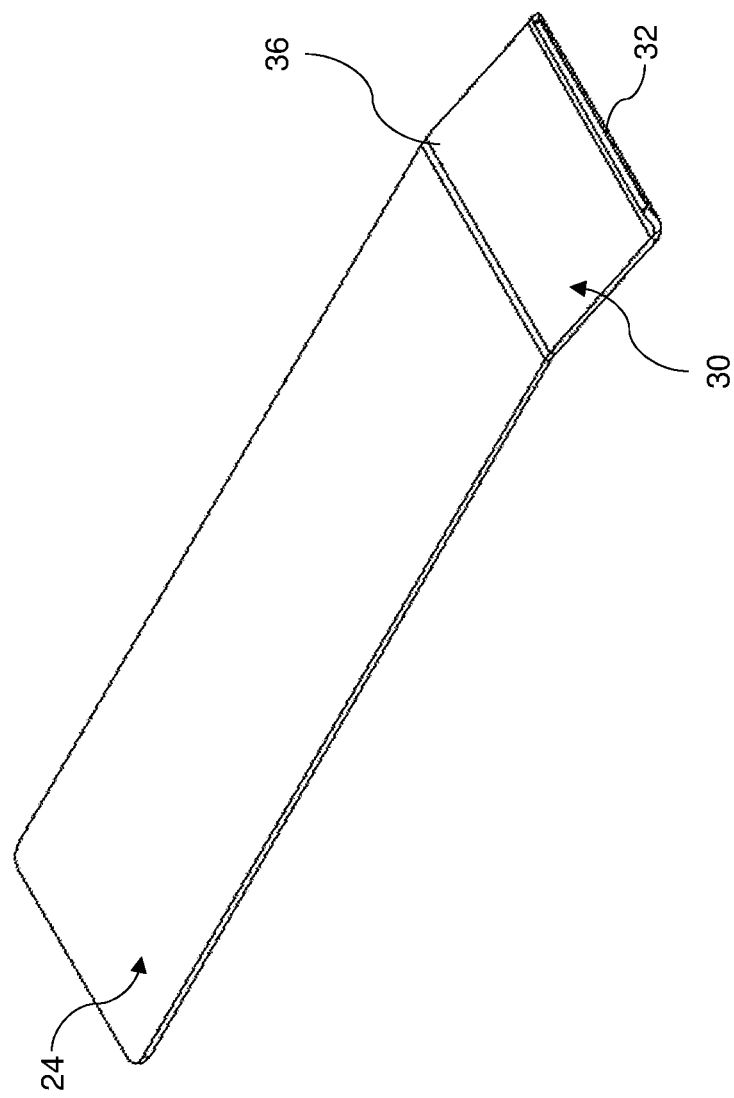
FIG. 2 is an exemplary embodiment of a retention means having a tab.
Figure 3:
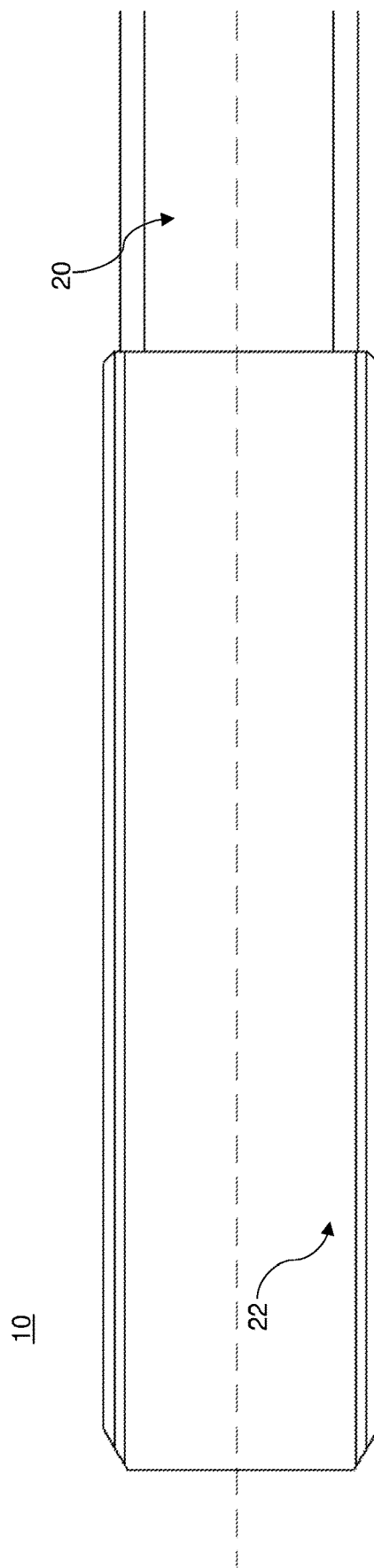
FIGS. 3 and 4 are exemplary embodiments of a light guide assembly including the retention means of FIG. 2.
Figure 4:
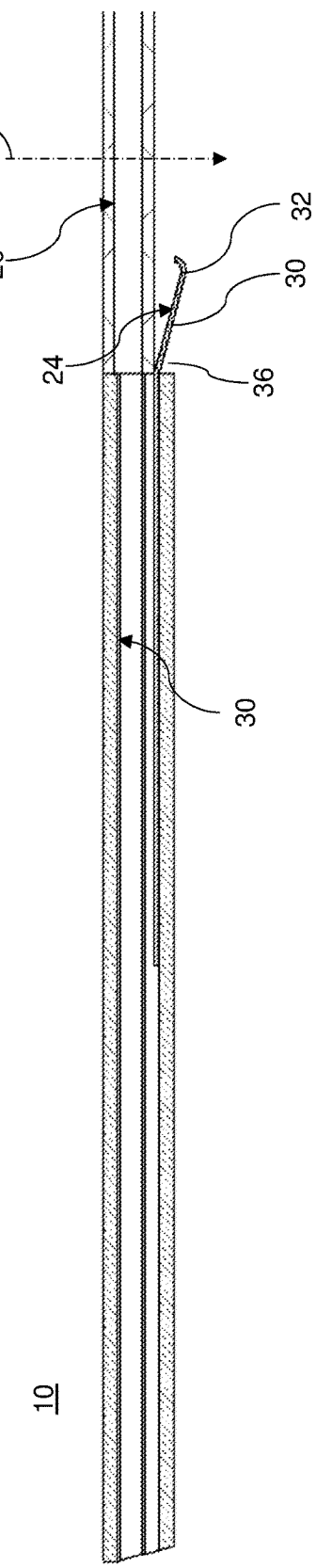
Figure 7:
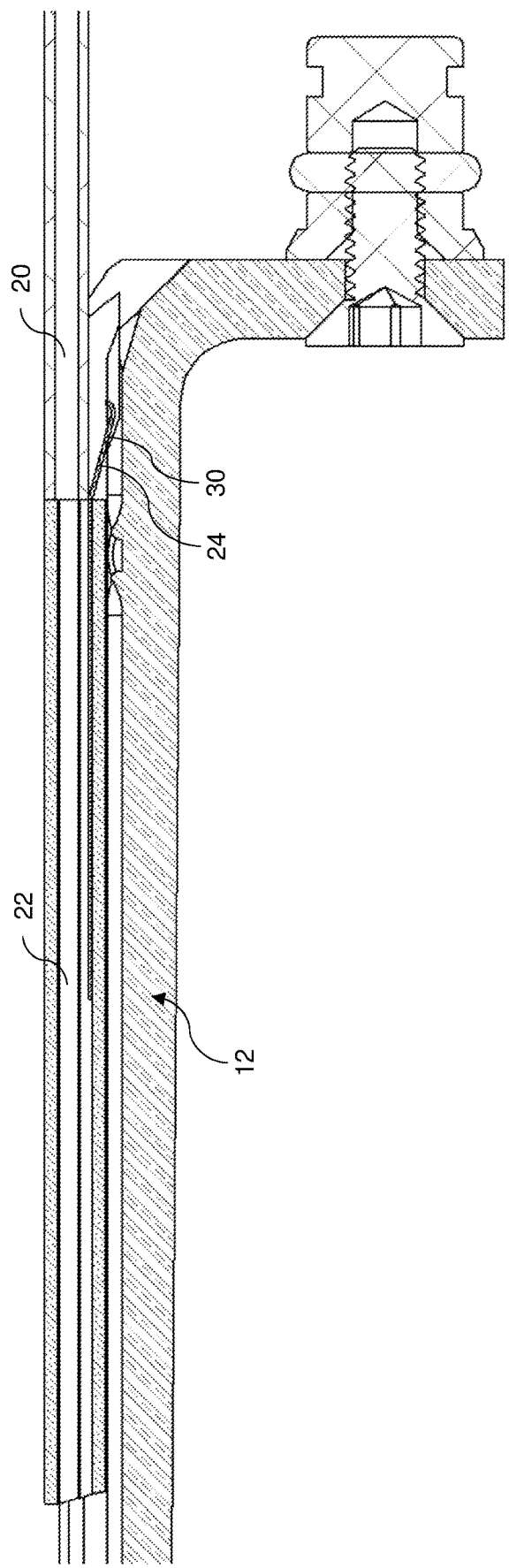
Figure 8:
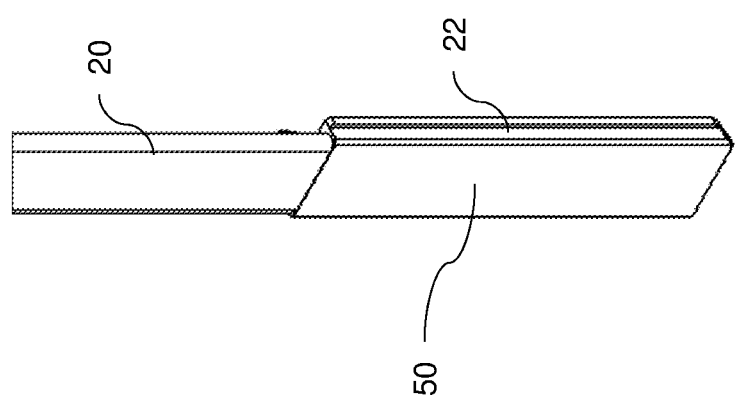
FIG. 8 is an alternative view of the light guide assembly of FIGS. 3 and 4.
Figure 11:
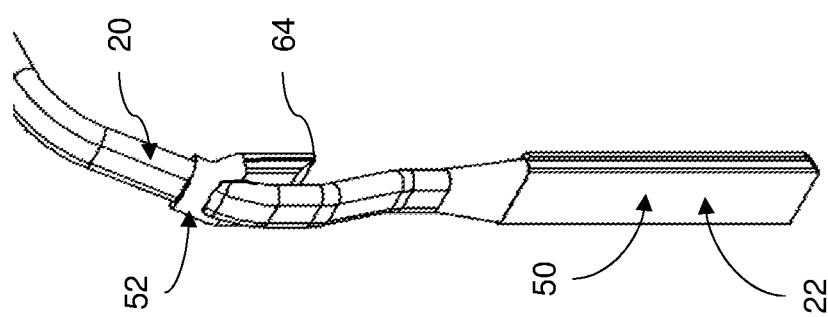
FIG. 11 depicts the light guide assembly of FIG. 10.
Figure 10:
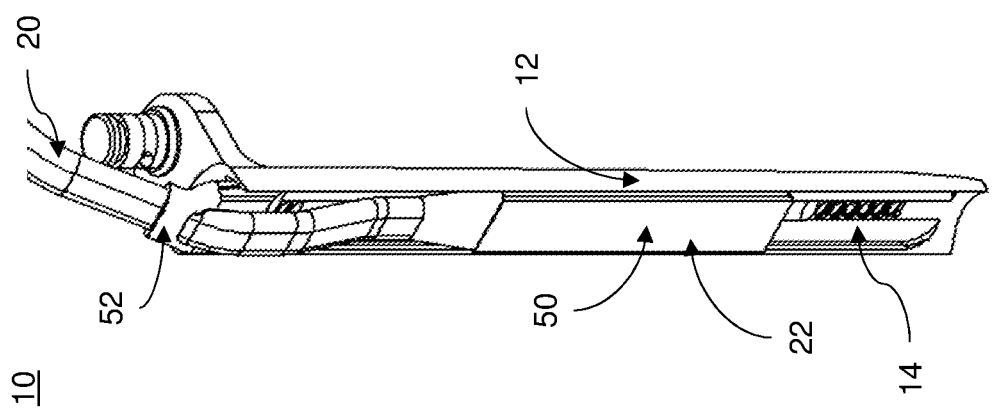
FIG. 10 depicts a light guide assembly including the retention means of FIGS. 9A-9C inserted into a channel of a retractor.
Figure 14:
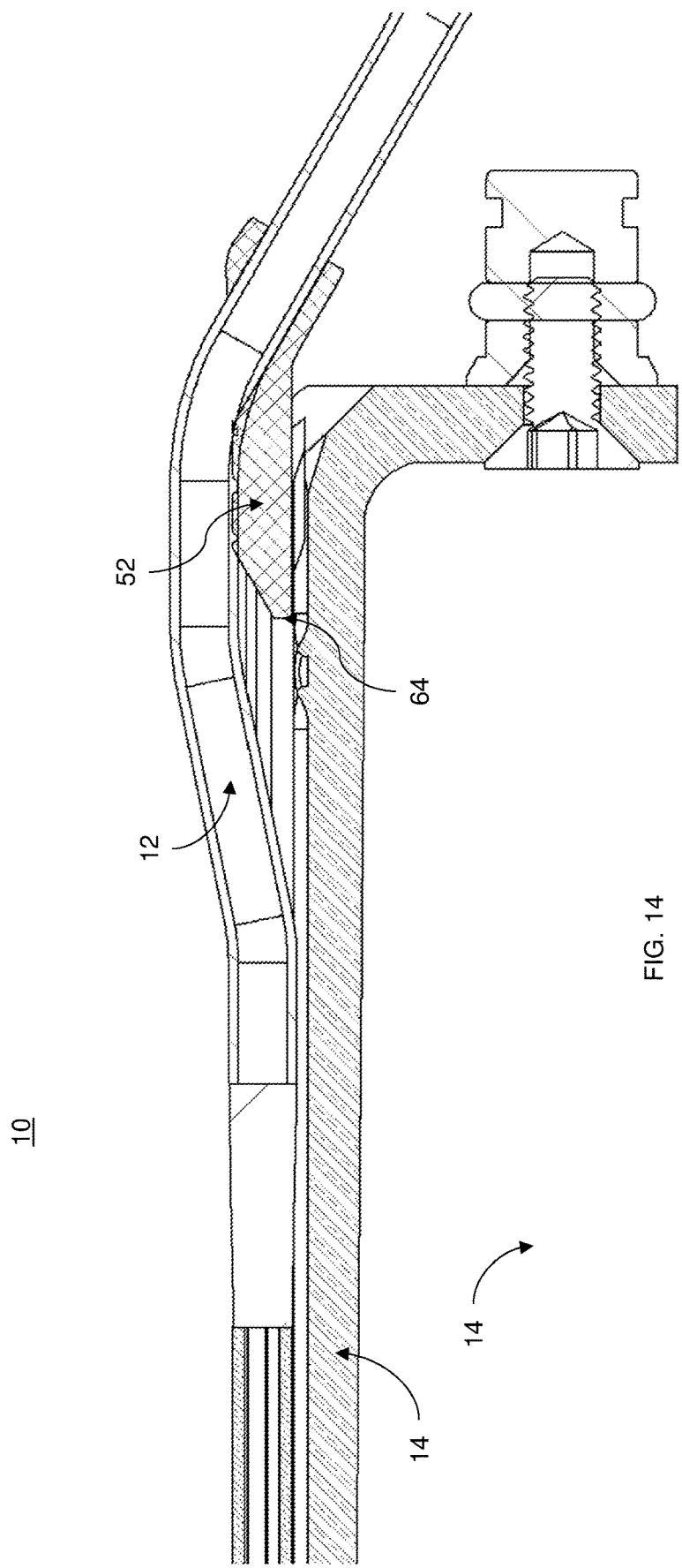
Figure 23:
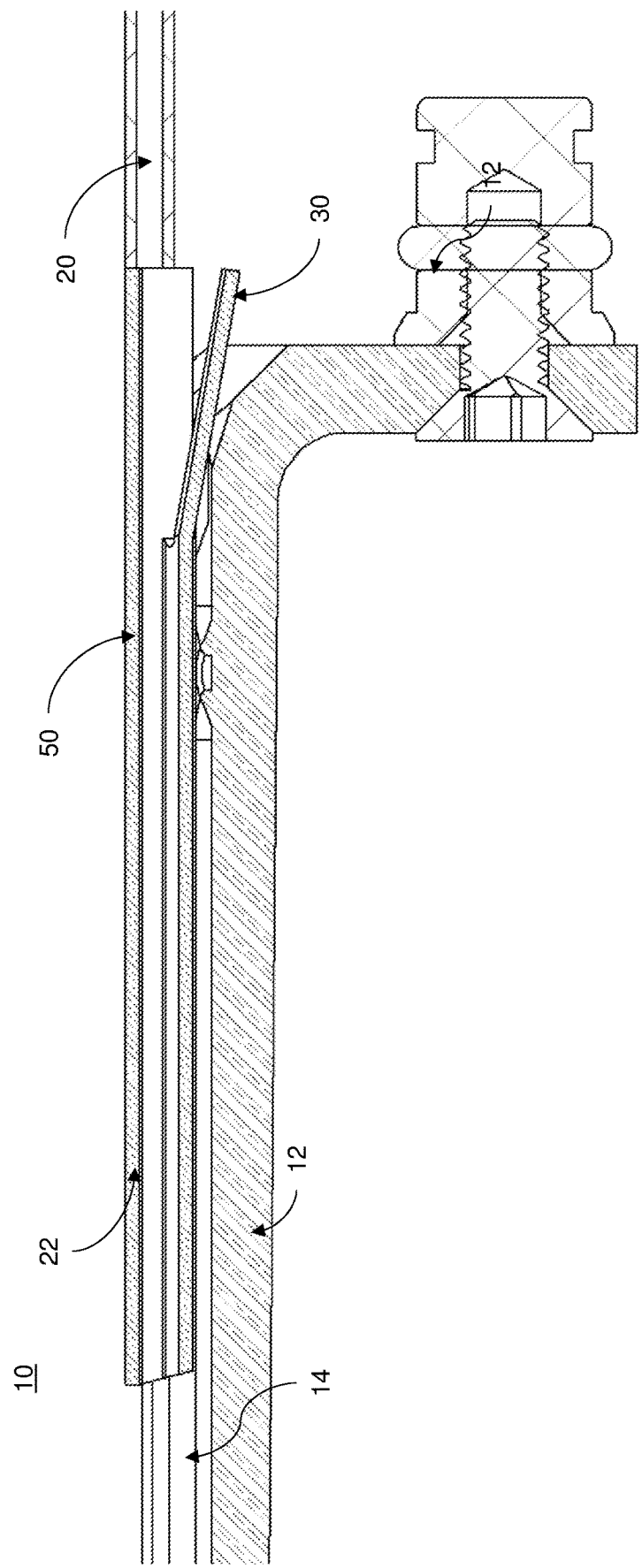
Figure 31:
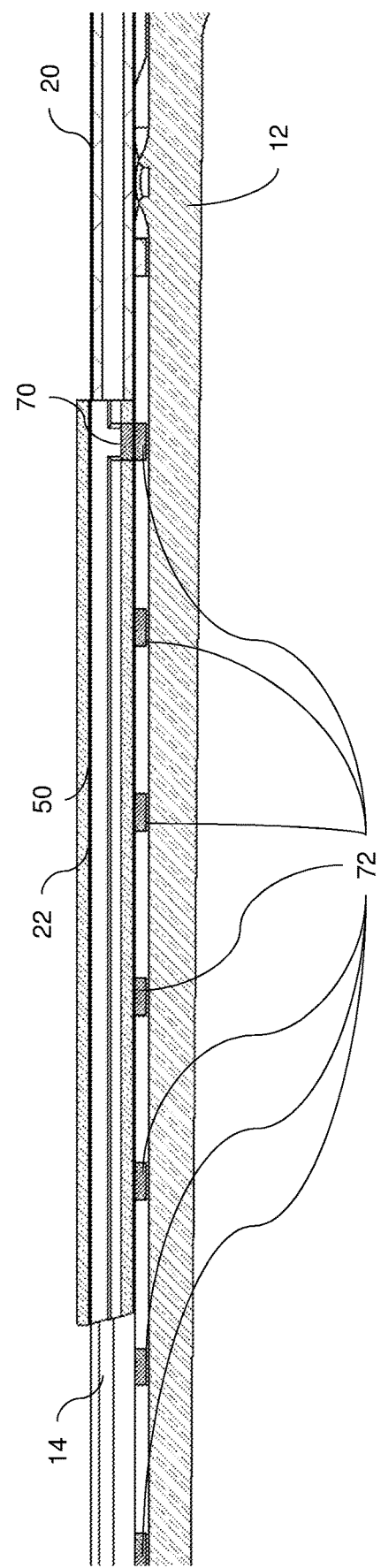
Figure 36:
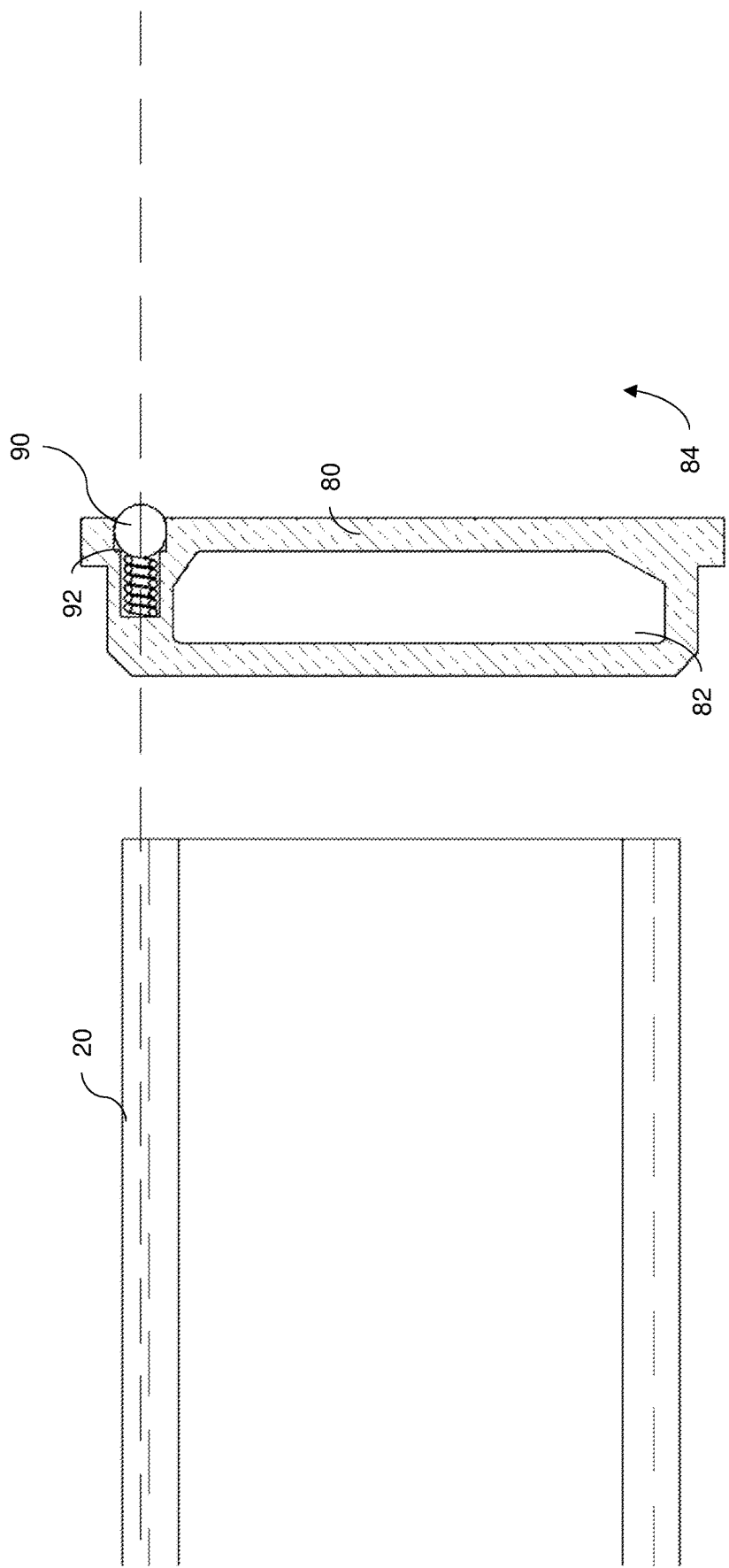
Figure 39:
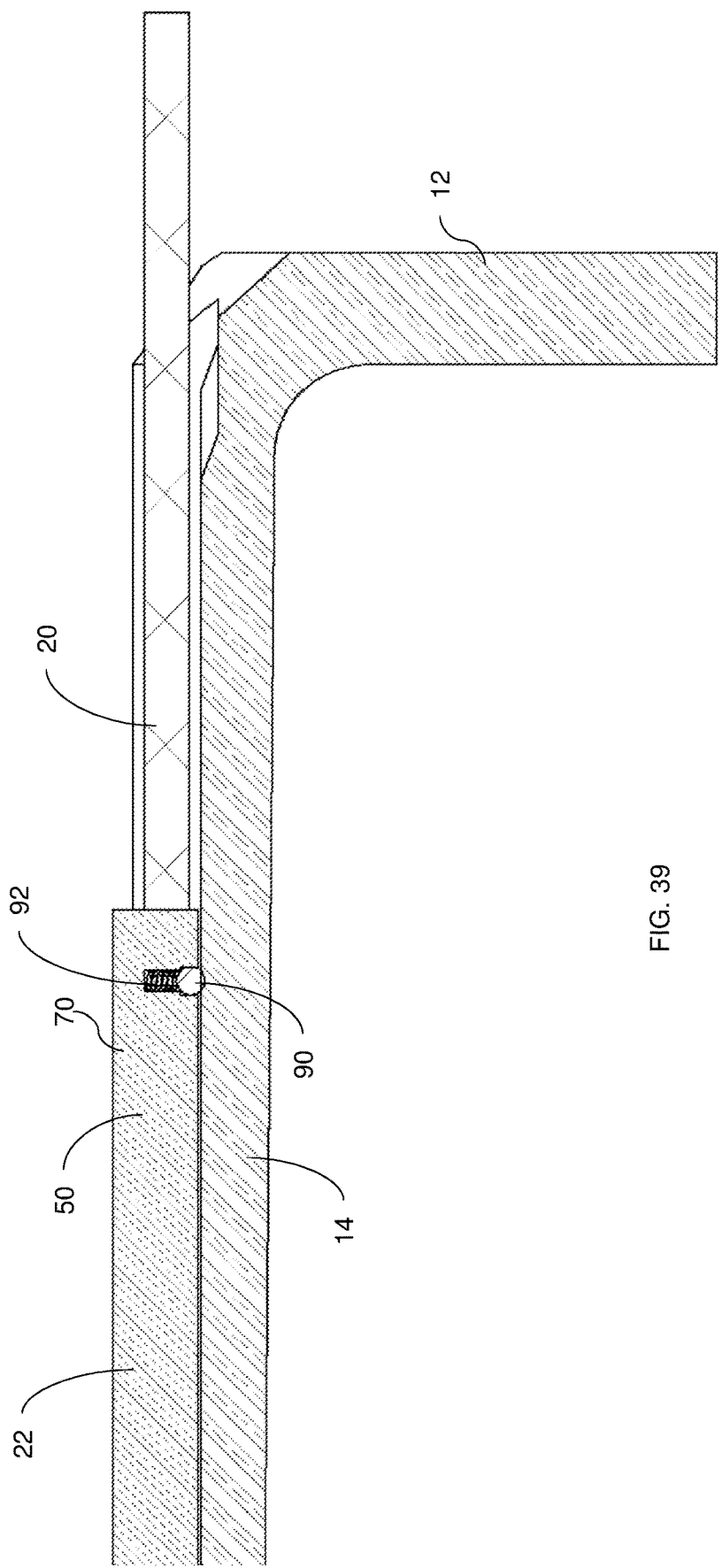
Figure 43:
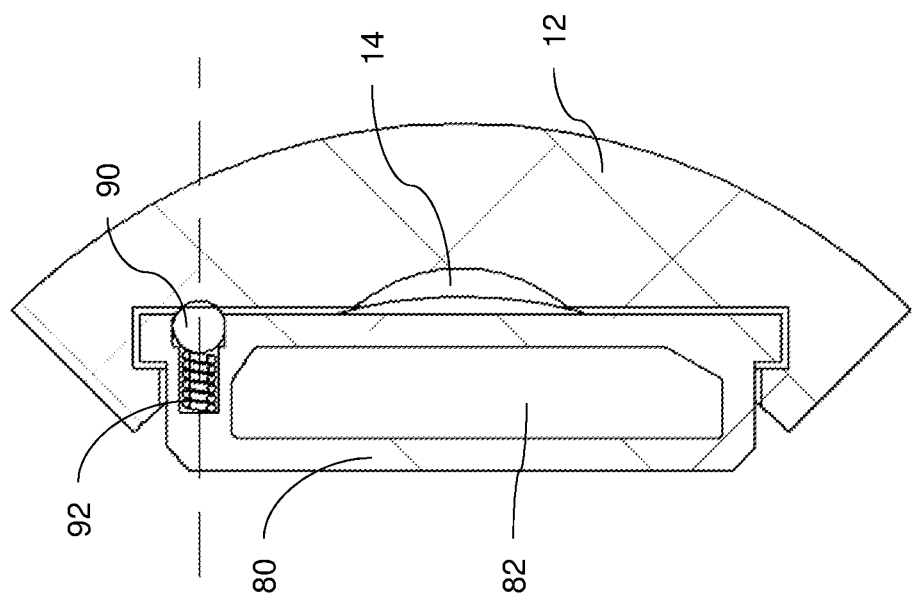
Figures 44A, 44B, 44C, 44D:
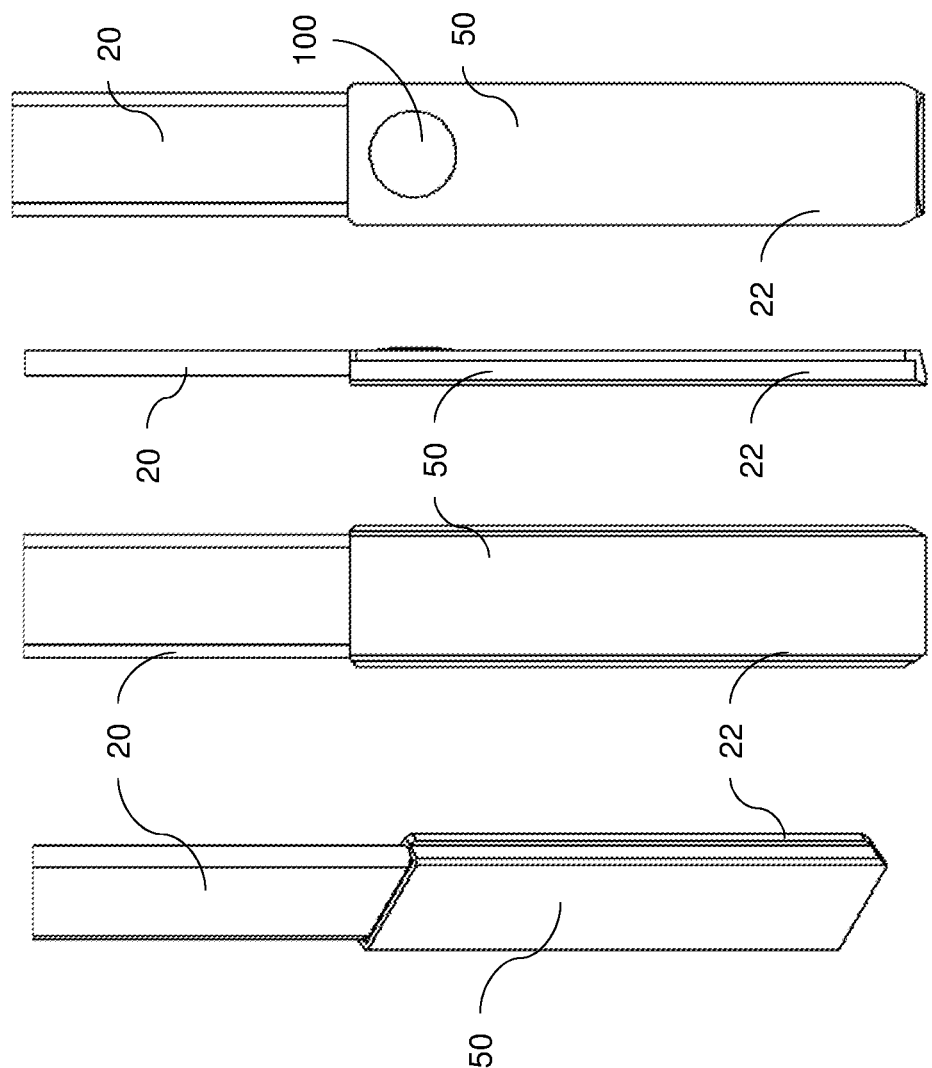
FIGS. 44A-44D depict an alternative embodiment of a retention means having a button.
Figures 47, 48:
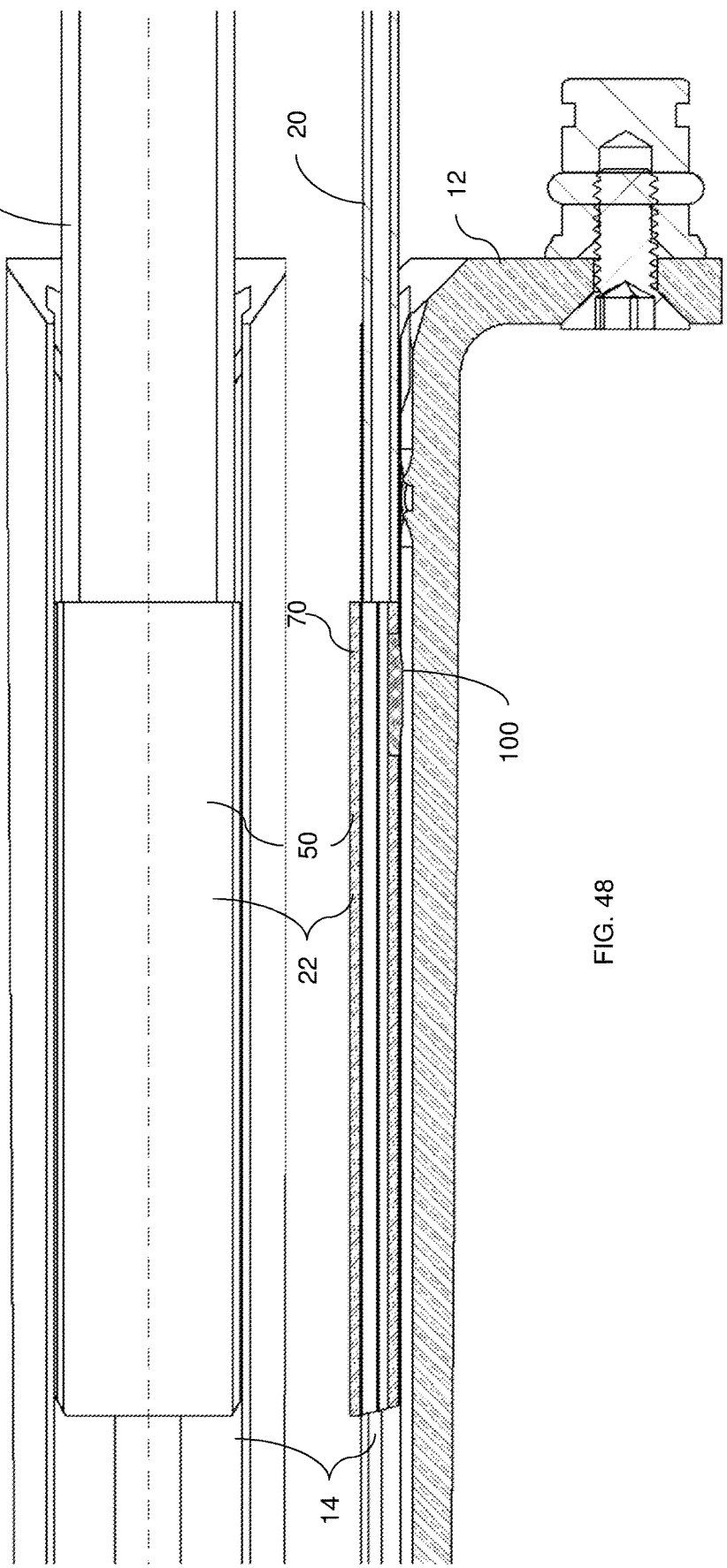
Figure 49:
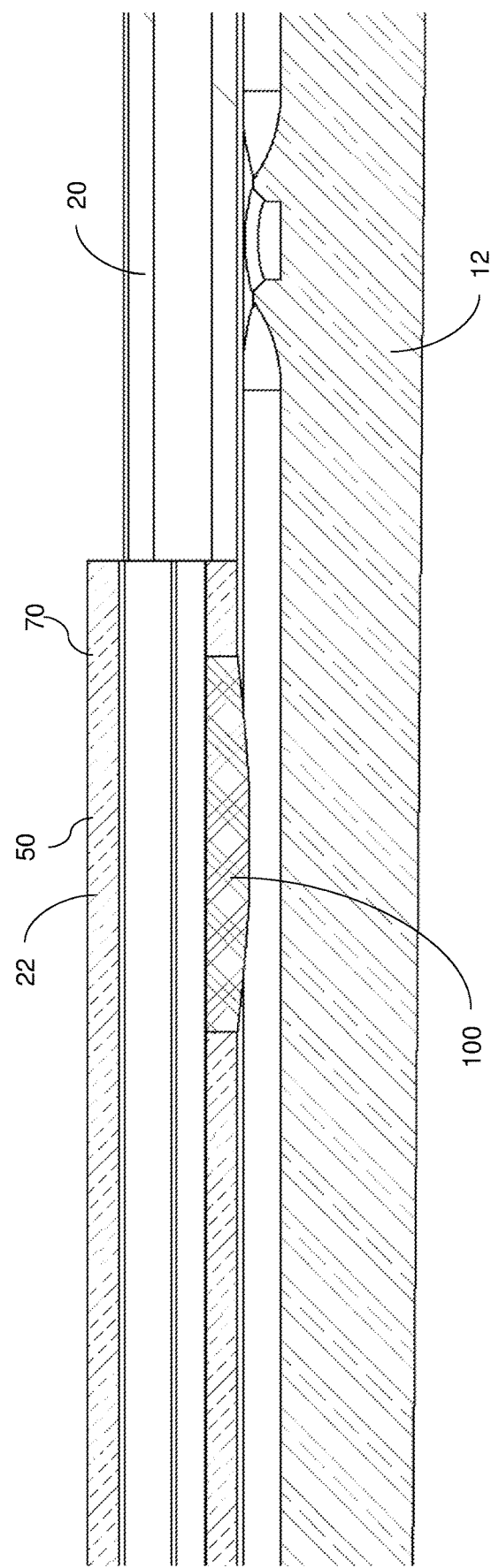

The present invention is now described in detail with reference to the drawings. In the drawings, each element with a reference number is similar to other elements with the same reference number independent of any letter designation following the reference number. In the text, a reference number with a specific letter designation following the reference number refers to the specific element with the number and letter designation and a reference number without a specific letter designation refers to all elements with the same reference number independent of any letter designation following the reference number in the drawings.

The present invention provides a light guide assembly for use with a retractor having a channel for slidably receiving an end portion of a light guide. The light guide assembly includes the light guide having the end portion and a retention means. The end portion is for slidably inserting into the channel of the retractor. The retention means is for releasably holding in position the end portion relative to the retractor.

Turning to FIG. 1 an exemplary light guide assembly 10 for use with a retractor 12 having a channel 14 is shown. The light guide assembly 10 includes a light guide 20 having an end portion 22 (for slidably inserting into the channel 14) and retention means 24 (also referred to as a retentor) for releasably holding in position the end portion 22 relative to the retractor 12.

Turning to FIGS. 2-8, a retention means 24 including a tab 30 is shown. The tab 30 is configured to contact the channel 14 during insertion of the end portion 22 into the channel 14, such that the force required to insert the end portion 22 into the channel 14 is increased.

The tab 30 may have a wedge shape, such that an apex 32 of the tab 30 is located farther from the end portion 22 than a proximal portion 36 of the tab 30. The apex 32 of the tab 30 may be located furthest from the light guide 20 along a radial direction 40. The proximal portion 36 of the tab 30 is inserted into the channel 14 prior to the apex 32 when the end portion 22 is slidably inserted into the channel 14.

Upon the tab 30 being slidably inserted into the channel 14, a force required to further slidably insert the tab 30 into the channel 14 increases until the apex 32 of the tab 30 enters the channel 14.

The tab 30 may comprise a bent steel tab with a radius at the same end can be inserted into the illuminator assembly as shown. This tab 30 is intended to contact the rear surface of the channel 14 in a retractor 12 and provide a frictional resistance to movement of the distal end of the surgical illuminator. The resistance to movement may be increased or decreased by changing material properties and/or geometry of the tab 30. This spring could be realized within or outside a sheathing surrounding the light guide 20.

Turning to FIGS. 9-18, the retention means 24 may comprise a wedge 52 configured to contact the channel 14 during insertion of the end portion 22 into the channel 14, such that the force required to insert the end portion 22 into the channel 14 increases upon the wedge 52 contacting the channel 14.

The wedge 52 may include a body 54 and an aperture 60. The body 54 has a receiving end 56 and a contacting end 58. The aperture 60 in the body 54 is located closer to the receiving end 56 than the contacting end 58. The contacting end 58 includes a contacting tip 64 configured to contact the channel 14 during insertion of the end portion 22 into the channel 14. The aperture 60 is configured to slide over the light guide 20, such that: (1) the wedge 52 is positioned distal to the end portion 22 of the light guide 20 such that the end portion 22 enters the channel 14 during insertion into the channel 14 prior to the wedge 52 entering the channel 14; and (2) the contacting tip 64 enters the channel 14 during insertion into the channel 14 prior to the aperture 60.

The body 54 of the wedge 52 may have a tapered profile, such that (during insertion of into the channel 14) the body 54 mates to the channel 14 and the tapered profile prevents the wedge 52 from being fully inserted into the channel 14.

Walls 62 of the aperture 60 may be oriented at an angle relative to a front face of the body 54, such that friction between the light guide 20 and the wedge 52 increases when the wedge 52 is inserted into the channel 14.

The wedge 52 may be shaped such that friction occurs between the wedge 52 and the light guide 20 at two interfaces: (1) between a sheathing around the light guide fiber and the edge of the wedge aperture 60 (due to the angle) and (2) between the walls 62 of the channel 14 of the retractor 12 and a ramped profile of the shoulders of the wedge 52.

The wedge 52 may also include a living hinge or cantilever spring configured such that a user may squeeze the wedge 52 and/or slide the wedge 52 out of the channel 14 to remove the wedge 52 from the channel 14.

The wedge 52 may be made from plastic or any other suitable material. The wedge 52 may have a slightly tapered profile at one end and a through hole at the opposite end can be slid onto the cable of the illuminator prior to installing the jacket at the distal end of the assembly. The tapered profile may mate to the channel 14 in the retractor 12 and may not be fully inserted into the channel 14 of the retractor 12 blade due to the taper. The through hole may be oriented at an angle relative to the front face of the tapered section resulting in additional friction between the cable of the illuminator and the plastic clip when the clip is seated in the retractor 12 (see images). The taper of the wedge 52, angle and size of the through hole, and cross sectional profile can be modified to increase or decrease friction for retention of the surgical illuminator in a retractor blade.

The wedge 52 (also referred to as a clip) may employ "squeeze to release" or "slide to release" functionality via a living hinge or cantilever spring feature molded into the part.

Turning to FIGS. 19-23, the end portion 22 of the light guide 20 may include a jacket 50 and the jacket 50 may include the retention means 24. For example, the retention means 24 may comprise a tab 30 and the tab 30 may be formed as part of the jacket 50.

For example, the tab 30 may be machined into a proximal end of a jacket 50 (e.g., an extrusion) used for channel type illuminators. The tab 30 may be intended to aid in illuminator retention via interfering with the rear surface of the retractor channel 14 much like a cantilever spring, but may present lower risk of being left in the surgical cavity because it is integrated with the jacket 50. The resistance to movement due to friction can be increased or decreased by changing the bend angle of the tab 30, changing the material properties of the jacket 50, or geometry of the tab 30.

Turning to FIGS. 24-31, the end portion 22 may include a jacket 50 and the jacket 50 may include the retention means 24. The retention means 24 may comprise a first magnet 70 configured to interact with a second magnet 72 included in the channel 14 of the extractor 12 such that a force required to insert the end portion 22 into the channel is increased by the interaction between the first magnet and the second magnet 72. The first magnet 70 and/or the second magnet 72 may have a length along the direction of insertion of the end portion 22 such that, upon the end portion 22 being slidably inserted into the channel 14, a force required to further slidably insert the end portion 22 into the channel 14 increases. The first magnet 70 and/or second magnet 72 may comprise a series of magnets spaced along a longitudinal axis of the jacket 50.

As described a jacket 50 (e.g., an extrusion) with an integrated magnet can be advanced into the retractor channel 14 and mate with another magnet that is integral to the retractor 12, providing resistance to change in position. The resistance to movement could be increased/decreased by altering the geometry, grade and position of the magnets. This would require a ferromagnetic material be employed in the retractor blade. Ferromagnetic elements could be used in a series, allowing the user to fix the surgical illuminator in discrete increments.

Turning to FIGS. 32-43, the end portion 22 of the light guide 20 may include a jacket 50 having a wall 80 separating an interior 82 and an exterior 84 of the jacket 50. The jacket 50 may include the retention means 24 comprising a plunger 90. The plunger 90 may be positioned within an opening 92 of the wall 80 of the jacket 50 such that, when positioned, the plunger 90 extends through the opening 92 of the wall 80 into the exterior 84 of the jacket 50. Upon the jacket 50 being slidably inserted into the channel 14, a portion of the plunger 90 extending into the exterior of the jacket 50 interacts with a wall of the channel 14 increasing a force required to further slidably insert the end portion 22 into the channel 14.

The plunger may include a spring 92 added to the jacket 50 (e.g., extrusion) to create an interference with the channel 14 of the retractor 12 and provide resistance to movement. The resistance could be tuned by altering the spring force within the plunger 90. The spring plunger could contact the rear of the retractor channel 14 (shown) or the sides of the channel 14.

Turning to FIGS. 44-49, the end portion 22 may include a jacket 50 and the jacket 50 may include the retention means 24 comprising a button 100. The button 100 may comprise a compressible material that, upon being slidably inserted into the channel 14, interacts with a wall of the channel 14 increasing a force required to further slidably insert the end portion 22 into the channel 14.

As described above, a compressible material may be introduced to a rear side of the jacket 50 (i.e., the side of the jacket 50 that is adjacent to a wall of the channel 14), to create an interference fit between the end portion 22 and the retractor 12. The resistance can be increased/decreased by adjusting material and/or geometric specs.

In another embodiment, a malleable insert may be preformed with a 180 degree radius just proximally to the jacket 50 within the sheathing/tubing surrounding the light guide 20. This could result in the additional friction necessary to maintain the light guide 20 position relative to the retractor 12 during an operation. Resistance to movement may be altered by altering material properties of the malleable and/or the geometry of the radius.

In the embodiments where the retention means 24 comprises a clip (e.g., the wedge 52 described above), the clip may slide along the length of the tubing surrounding the light guide 20 as shown above. The clip may also attach to the frame of the retractor itself and could be stamped metal or molded plastic to manage the cabling and/or prevent unintended movement of the distal end of the surgical illuminator.

The retention means 24 may be radio-opaque to prevent loss within the patient or radiolucent to allow improved visualization via intraoperative fluoroscopy.

The surgical retractor 12 may have a single leg, may be bifurcated, or may have more than two legs that convey light to the operative site. One or all legs of the surgical illuminator may incorporate one of the retention features listed above.

Any and all ranges and ratio limits disclosed in the specification and claims may be combined in any manner. Unless specifically stated otherwise, references to "a," "an," and/or "the" may include one or more than one, and that reference to an item in the singular may also include the item in the plural.

Although the invention has been shown and described with respect to a certain embodiment or embodiments, equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

The invention claimed is:

1. A light guide assembly for use with a retractor having a channel, the light guide assembly comprising:
   a light guide having an end portion for slidably inserting into the channel of the retractor; and
   a retentor for releasably holding in position the end portion relative to the retractor, the retentor comprising a wedge configured to contact the channel during insertion of the end portion into the channel, the wedge including:
   a body; and
   a throughbore in the body configured to slide over the light guide, such that the wedge is positioned distal to the end portion of the light guide such that the end portion enters the channel during insertion into the channel prior to the wedge entering the channel.

2. The light guide assembly of claim 1, wherein the wedge is configured such that a force required to insert the end portion into the channel increases upon the wedge contacting the channel.

3. The light guide assembly of claim 2, wherein the body of the wedge includes:
   a receiving end and a contacting end wherein:
      the throughbore in the body located closer to the receiving end than the contacting end;
      the contacting end includes a contacting tip configured to contact the channel during insertion of the end portion into the channel; and
      the contacting tip enters the channel during insertion into the channel prior to the throughbore.

4. The light guide assembly of claim 1, wherein the body of the wedge has a tapered profile, such that:
   during insertion into the channel, the body mates to the channel and the tapered profile prevents the wedge from being fully inserted into the channel.

5. The light guide assembly of claim 1, wherein walls of the throughbore are oriented at an angle relative to a front face of the body, such that friction between the light guide and the wedge increases when the wedge is inserted into the channel.

6. The light guide assembly of claim 1, wherein the wedge includes a living hinge or cantilever spring configured such that a user may squeeze the wedge and/or slide the wedge out of the channel to remove the wedge from the channel.

7. A retractor assembly comprising:
   a retractor and a light guide, wherein:
      the retractor includes a blade having a channel for slidably receiving the light guide;
      the light guide includes a retentor for releasably holding the light guide in position in the channel; and
      the retentor including a wedge configured to contact the channel during insertion of the end portion into the channel, the wedge including:
      a body; and
      a throughbore in the body configured to slide over the light guide wherein walls of the throughbore are oriented at an angle relative to a front face of the body such that friction between the light guide and the wedge increases when the wedge is inserted into the channel.

8. A method of adjustably positioning a light guide in relation to a retractor having a channel for slidably receiving an end portion of the light guide, the method comprising the steps of:
   slidably positioning the light guide into the channel; using a retentor for releasably maintaining the position of the light guide within the channel; and
   increasing an amount of friction between the light guide and a wall of a throughbore defined by a wedge portion of the retentor to releasably hold in position the light guide relative to the retentor when the wedge is inserted into the channel.

* * * * *